United States Patent [19]

Malpass et al.

[11] 4,341,910
[45] Jul. 27, 1982

[54] PREPARATION OF UNSATURATED ALCOHOLS

[75] Inventors: Dennis B. Malpass, La Porte; G. Scott Yeargin, Pasadena, both of Tex.

[73] Assignee: Texas Alkyls, Inc., Deer Park, Tex.

[21] Appl. No.: 6,323

[22] Filed: Jan. 25, 1979

[51] Int. Cl.³ .................... C07C 29/00; C07C 33/025
[52] U.S. Cl. ........................... 568/878; 260/448 A; 568/840
[58] Field of Search ....................................... 568/878

[56] References Cited

U.S. PATENT DOCUMENTS 3,093,691 6/1963 McClaflin et al. ................ 568/878

OTHER PUBLICATIONS

Zweifel et al., "J. Am. Chem. Soc.," vol. 89, (1967), pp. 5085–5086.
Malpass et al., "J. Org. Chem.," vol. 42, (1977), pp. 2712–2715.

Primary Examiner—Joseph E. Evans
Attorney, Agent, or Firm—Joel G. Ackerman

[57] ABSTRACT

A process for the production of cis and trans isomers of compounds having the formula

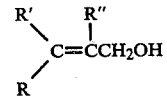

in which R, R' and R" are independently hydrogen or alkyl groups having from 1 to 20 carbon atoms, comprising
(a) reacting the corresponding cis or trans isomer of a compound having the formula

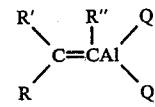

in which Q is an alkyl group having from 1 to 20 carbon atoms, with paraformaldehyde and
(b) hydrolyzing the resulting product to produce the unsaturated alcohol.

7 Claims, No Drawings

PREPARATION OF UNSATURATED ALCOHOLS

BACKGROUND AND PRIOR ART

This invention relates to a process for the ultimate production of unsaturated alcohols having the formula

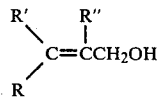

in which R, R' and R" are independently hydrogen or alkyl groups having from 1 to 20 carbon atoms each. Such compounds will be referred to hereinafter as 2-alken-1-ols. This invention also relates to novel intermediates for production of such compounds and to novel processes for producing such compounds and intermediates.

A number of compounds of this type, in both cis and trans isomers, are already known and have been found useful as chemical intermediates and as flavoring and other sensory agents. For example, the compound trans-2-hexen-1-ol is useful in flavoring strawberry and orange juices.

As will be discussed hereinafter, this application finds greatest use in the production of cis-2-alken-1-ols. Such compounds have been prepared by various methods as described, for example, in the article by Delady, Bull. Soc. Chem., Vol. 5, No. 3 (1936) pp. 2375–2382, and particularly on page 2380 (preparation of 2-decen-1-ol by reaction of β-heptylylallyl acetate with caustic soda) and Crombie, et al., J. Chem. Soc., 1955, pp. 4244–4249 (hydrogenation of hex-2-yn-1-ol). Another process, rather complicated in nature, is described in a latter by Zweifel, et al., J. Am. Chem. Soc., Vol. 89, pp. 5085–5086 (1967). In this process, an acetylenic compound is reacted with a dialkylaluminum hydride and an alkyllithium compound to produce an intermediate trans-vinylalanate compound which can then be reacted with paraformaldehyde to produce cis-α,β-unsaturated alcohols.

In an article by Malpass, et al., J. Org. Chem., Vol. 42, pp. 2712–2715 (1977) and in U.S. Pat. No. 4,069,260, there is described a process for production of cis-3-alken-1-ols by reaction of an unsaturated aluminum alkyl with various alkylene epoxides. Such a process provides for the production of such alkenols directly from the corresponding cis-substituted aluminum compounds, rather than by the complicated methods heretofore used. The letter by Zweifel, et al. states that in their process, an isomeric shift occurs in that reaction of the trans-vinylalanates formed using the alkyl lithium compounds, with paraformaldehyde, results in cis-unsaturated alcohols.

It would also be desirable to provide a process by which trans-unsaturated alcohols can be produced from the corresponding trans-unsaturated aluminum compounds.

SUMMARY OF THE INVENTION

This invention comprises a process for the production of compounds selected from the group consisting of cis and trans isomers of compounds having the formula

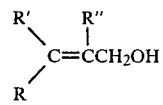

in which R, R' and R" are independently hydrogen or alkyl groups having from 1 to 20 carbon atoms, comprising:
(a) reacting a corresponding cis or trans isomer of a compound having the formula

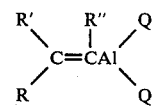

in which R, R' and R" are as defined above and Q is an alkyl group having from 1 to 20 carbon atoms with paraformaldehyde and
(b) hydrolyzing the resulting product to obtain the desired compound.

In accordance with this process, the desired cis- and trans-isomers of these compounds can be prepared directly from the corresponding unsaturated aluminum compounds.

Also included within the scope of this invention are novel compounds having the formula

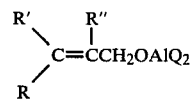

in which R, R', R" and Q are as defined above. These compounds are prepared by the first step of the above-mentioned process and are useful as intermediates for producing the final cis- or trans-2-alken-1-ols.

DETAILED DESCRIPTION OF THE INVENTION

The starting materials for the process of this invention are alkenyl-aluminum compounds of the formula

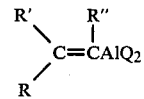

in which R, R' and R" are independently hydrogen or alkyl groups having from 1 to 20 carbon atoms and Q is an alkyl group having from 1 to 20 carbon atoms. Such compounds can be obtained in a number of ways, but a convenient method for their preparation is shown in the article of Malpass, et al. referred to above, namely by either the reaction of a trialkyl aluminum compound with acetylene or a substituted acetylene or of a dialkyl-aluminum hydride with a substituted acetylene. Examples of such reactions are

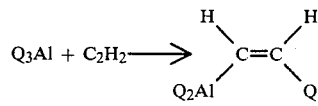

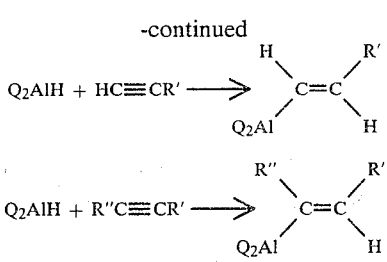

It is preferable that all the alkyl components of the trialkyl aluminum or dialkyl aluminum hydrides are identical so that a mixture of products is not formed. These alkyl (Q) groups may be straight or branched chain; in using branched chain compounds it would not be desirable to utilize those secondary-alkyl compounds which are known in the art to be somewhat unstable.

The addition therefore, of the aluminum compound to the acetylenic compounds occurs as cis addition across the triple bond. When a trialkyl aluminum compound is reacted with acetylene or a substituted acetylene, a cis-olefinically unsaturated aluminum compound is obtained. The reaction of a dialkylaluminum hydride with a substituted acetylene, on the other hand, produces a trans-olefinically unsaturated aluminum compound.

The alkenyl aluminum compound, however obtained, is then reacted with paraformaldehyde in the presence of a suitable solvent, such as n-hexane, producing an intermediate alkenoxy aluminum compound having the formula

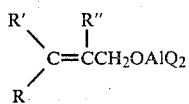

in which R, R', R" and Q are as defined above. In this step, the paraformaldehyde selectively reacts with the vinyl carbon-aluminum bond and not with any other portion of this molecule. The temperature for this reaction is generally from about $-20°$ C. to about $+120°$ C., preferably from about 10° C. to about 50° C. This alkenoxy aluminum compound is then hydrolyzed with acid, for instance with a mineral acid such as sulfuric acid, to produce the corresponding 2-alken-1-ol.

For each mole of alcohol there are also produced two moles of an alkane (formed from the Q groups bound to the aluminum) and one or more salts of aluminum. To purify the alcohol, the organic layer containing the product and solvent is separated. The organic layer is then distilled in a vacuum-jacketed packed column. Residual water, solvent and low boiling side products are first removed by fractionation. The product fraction is removed as a portion between 5° C. above and below the boiling point of the alcohol. This procedure was sufficient in some cases to produce a product of 91–93% purity. A more highly pure compound (96–99% or higher purity) can be obtained by subjecting the product to further distillation.

The following examples are representative of processes according to this invention.

EXAMPLE 1

Into a nitrogen blanketed 5-liter flask equipped with a reflux condenser, funnel and stirrer, were introduced 315 grams (10.50 moles) of paraformaldehyde, followed by 500 milliliters of dry n-hexane. There was then added 1817 grams (9.97 moles) of di-n-propylpentenylaluminum (prepared from tri-n-propylaluminum and acetylene) over a period of 10 hours, with the reaction temperature maintained at 50° C. The reaction mixture was heated and stirred for an additional hour under reflux at 60° to 62° C., and then cooled to room temperature.

Hydrolysis of the reacted material was performed in the following fashion. Two liters of 20% sulfuric acid solution was introduced into an apparatus similar to that used for the reaction, with the temperature maintained at about $-15°$ C. by use of a silicone oil bath and dry ice in the gas condenser. The crude reaction product was introduced into the stirred acid at a rate of about 5 milliliters per minute. The hydrolysis required about 8 hours for completion. The organic and aqueous phases were then removed and separated and the aqueous layer was washed twice with 100-milliliter portions of hexane. The hexane washes were combined with the organic phase, which was then filtered to remove suspended matter. The combined organic phase was washed with an equal volume of distilled water.

The crude product solution was distilled to recover the desired alcohol. A three-foot silvered vacuum-jacketed packed column was used for this procedure. Pressure was maintained at 31 mm Hg. Residual water, solvent and low-boiling side products were first removed by fractionation, then the product was removed as the fraction boiling from 71°–81° C. There was obtained 626 grams (6.25 moles) of cis-2-hexan-1-ol (62.7% of theoretical yield), having a purity of 91%. Identity of the compound was confirmed by ir (infrared) and nmr (nuclear magnetic resonance) spectral analysis. Redistillation of the product using a larger packed column resulted in several fractions totaling 464 grams with purities of 99.2% or greater.

EXAMPLE 2

Similarly to the procedure described in Example 1, a 25% slurry of 243 grams (8.00 moles) paraformaldehyde in n-hexane was treated with 1069 grams (7.62 moles) of diethyl butenylaluminum (prepared from triethylaluminum and acetylene). Distillation of the hydrolysis product was performed under 25 mm Hg. The product fraction was removed at 56°–66° C. There was obtained 300 grams (3.48 moles) of cis-2-penton-1-ol (45.8% of theoretical yield), having a purity of 93%. Identity of the compound was confirmed by ir and nmr spectral analyses.

EXAMPLE 3

Similarly to the procedure described in Example 1, a 25% slurry of 144 grams (4.80 moles) of paraformaldehyde in n-hexane was treated with 1083 grams (4.59 moles) is di-n-octyl decenyl aluminum (prepared from tri-n-octyl aluminum and acetylene). Distillation of the hydrolysis product was performed under 2 mm Hg. The product fraction was removed at 85°–95° C. There was obtained 210 grams (1.25 moles) of cis-2-undecen-1-ol (27.2% of theoretical yield), having a purity of 91%. Identity of the compound was confirmed by ir and nmr spectral analyses.

EXAMPLE 4

Similarly to the procedure described in Example 1, a 17% slurry of 159 grams (5.29 moles) of paraformaldehyde in n-hexane was treated with 1488 grams (3.12 moles) of di-n-decyl dodecenyl aluminum (obtained from tri-n-decyl aluminum and acetylene). Distillation of the hydrolysis product was performed under 0.35 mm Hg. The product fraction was removed at 89°-99° C. There was obtained 133 grams (0.67 moles) of cis-2-tridecen-1-ol (13.3% of theoretical yield), having a purity of 92%. Identity of the compound was confirmed by ir and nmr spectral analyses.

EXAMPLE 5

Similarly to the procedure described in Example 1, a 54% slurry of 18.5 grams (0.611 mole) of paraformaldehyde in n-hexane was treated with 123.5 grams (0.587 mole) of trans-diisobutyl-1-pentenylaluminum (prepared from diisobutyl aluminum hydride and 1-pentyne). Distillation of the hydrolysis product was performed under 12 mm Hg at a pot temperature of 68°-73° C. (rate of boiling was too low to obtain an accurate overhead temperature). There was obtained 15 grams (0.145 moles) of trans-2-hexen-1-ol (24.8% of theoretical yield) having a purity of 96.1%. Identity of the compound was confirmed by ir and nmr spectra using a known sample of the desired compound.

What is claimed is:

1. A process for the production of compounds selected from the group consisting of cis and trans isomers of compounds having the formula

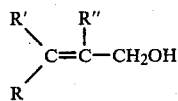

in which R, R' and R" are independently hydrogen or alkyl groups having from 1 to 20 carbon atoms, comprising (a) reacting the corresponding cis or trans isomer of a compound having the formula

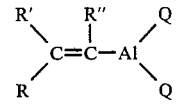

in which R, R' and R" are as defined and Q is an alkyl group having from 1 to 20 carbon atoms, with paraformaldehyde and (b) hydrolyzing the product of step (a) in the presence of an acid.

2. A process according to claim 1 in which the product of step (b) is a cis-2-alken-1-ol.

3. A process according to claim 1 in which the product of step (b) is a trans-2-alken-1-ol.

4. A process according to claim 1 in which R' and R" are both hydrogen.

5. A process according to claim 1 in which step (a) is conducted at a temperature of from about −20° C. to about +120° C.

6. A process according to claim 1 in which step (a) is conducted at a temperature of from about 10° C. to about 50° C.

7. A process according to claim 1 further comprising distilling the product of step (b) and recovering a fraction boiling between 5° C. and above and below the boiling point of the desired product.

* * * * *